(12) United States Patent
Arimori et al.

(10) Patent No.: US 6,387,672 B1
(45) Date of Patent: May 14, 2002

(54) PHOTO-INDUCED ELECTRON TRANSFER FLUORESCENT SENSOR MOLECULES

(75) Inventors: Susumu Arimori, Bath; Tony D. James, Birmingham, both of (GB)

(73) Assignee: Beckman Coulter, Inc., Fullerton, CA (US)

(*) Notice: Subject to any disclaimer, the term of this patent is extended or adjusted under 35 U.S.C. 154(b) by 0 days.

(21) Appl. No.: 09/729,332

(22) Filed: Dec. 4, 2000

(51) Int. Cl.$^7$ .......................... C12N 9/00; G01N 21/76; G01N 33/566; C09K 11/06
(52) U.S. Cl. .................. 435/183; 436/172; 436/501; 436/546; 252/301.16; 252/301.22
(58) Field of Search ................. 436/501, 172, 436/546; 252/301.16, 301.22; 435/183

(56) References Cited

U.S. PATENT DOCUMENTS

| | | | |
|---|---|---|---|
| 4,496,722 A | 1/1985 | Gallop et al. .................. 544/69 |
| 5,212,099 A | 5/1993 | Marcus ........................ 436/172 |
| 5,342,789 A | 8/1994 | Chick et al. ................. 436/501 |
| 5,501,949 A | 3/1996 | Marshall ........................ 435/5 |
| 5,503,770 A | 4/1996 | James et al. ............. 252/301.16 |
| 5,763,238 A | 6/1998 | James et al. ................. 436/172 |
| 5,798,083 A | 8/1998 | Massey et al. ................. 422/52 |
| 6,002,954 A | * 12/1999 | Antwerp et al. ............. 600/317 |

FOREIGN PATENT DOCUMENTS

| | | | |
|---|---|---|---|
| DE | 44 39 783 A1 | 4/1996 | ............. C07F/5/02 |
| EP | 0 729 962 B1 | 9/1996 | ............. C07F/5/02 |

OTHER PUBLICATIONS

Sandanayake et al.("Two Dimensional Photoinduced Electron Transfer(PET) Fluorescence Sensor for Saccharides", Chem. Lett., 1995, 503–504.*

"Novel Saccharide–Photoinduced Electron Transfer Sensors Based on the Interaction of Boronic Acid and Maine," Tony D. James et al., *J. Am. Chem. Soc.* vol. 117, No. 35, 1995, pp. 8982–8987.

"Fluorescence and CD Spectroscopic Sugar Sensing by a Cyanine–appended Diboronic Acid Probe," Masayuki Takeuchi et al., *Tetrahedron*, vol. 52, No. 4, pp. 1195–1204, 1996.

"Synthetic Receptors," James H. Hartley et al., *J. Chem. Soc., Perkin Trans.* 1, 2000, pp. 3155–3184.

* cited by examiner

*Primary Examiner*—W. Gary Jones
*Assistant Examiner*—B J Forman
(74) *Attorney, Agent, or Firm*—William H. May; Arnold Grant; Hogan & Hartson

(57) ABSTRACT

Disclosed is a modular fluorescence sensor having the following general formula:

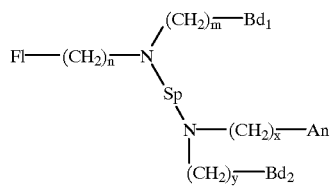

where Fl is a fluorophore, N is a nitrogen atom, $B_{d1}$ and $B_{d2}$ are independently selected binding groups, Sp is an aliphatic spacer, and An is an anchor group for attaching the sensor to solid substrates. n=1 or 2, m=1 or 2, x is an integer, and y=1 or 2. The binding groups are capable of binding an analyte molecule to form a stable 1:1 complex. In a preferred embodiment, the $B_{d1}$ is $R_1$—B(OH)$_2$ and $B_{d2}$ is $R_2$—B(OH)$_2$. $R_1$ and $R_2$ are aliphatic or aromatic functional groups selected independently from each other and B is a boron atom. The present invention also provides methods of synthesizing a modular fluorescence sensor and its use in labeling solid substrates.

28 Claims, 2 Drawing Sheets i) benzaldehyde, THF/EtOH, r.t., 24h, ii) NaBH$_4$, THF, r.t., 7h, 74% (2 steps total),
iii) 1-pyrenealdehyde, THF/MeOH, r.t., 20h, 93%, iv) NaBH$_4$, MeOH, r.t., 3h, 92%
v) 2, K$_2$CO$_3$, MeCN, reflux, 20h, vi) THF/water, r.t., 3h, 35% i) benzaldehyde, THF/EtOH, r.t., 24h, ii) NaBH$_4$, THF, r.t., 7h, 74% (2 steps total),
iii) 1-pyrenealdehyde, THF/MeOH, r.t., 20h, 93%, iv) NaBH$_4$, MeOH, r.t., 3h, 92%
v) 2, K$_2$CO$_3$, MeCN, reflux, 20h, vi) THF/water, r.t., 3h, 35%

PHOTO-INDUCED ELECTRON TRANSFER FLUORESCENT SENSOR MOLECULES

BACKGROUND OF THE INVENTION

1. Area of the Art

The invention relates generally to fluorescence sensor molecules and specifically to a new group of modular fluorescence sensor molecules.

2. Description of the Prior Art

Numerous assay methods have been developed for the detection and quantitative determination of analytes contained in biochemical samples. A substantial portion of the currently used assay methods relies on specific binding reactions between analytes and assay reagents. The analytes may be large complex molecules, such as proteins, viruses, viral antigens, bacterial cells, cell surface receptors, enzymes, hormones, polysaccharides, glycoproteins, lipoproteins, or small haptenic molecules, such as peptides, certain hormones, therapeutic drugs, and drugs of abuse, to name a few.

The binding assays can be divided into two major groups based on their format: homogeneous and heterogeneous assays. Homogeneous assays are based on a single-phase reaction between analyte and assay reagents. Heterogeneous assays, typically, involve binding of an analyte contained in the liquid sample to assay reagents, which are attached to a solid support. Various materials have been used as support surfaces, including glass rods, glass beads, silica impregnated strips, glass fiber, and microparticles.

Dyes in general, and fluorescent dyes in particular, are commonly utilized in both homogeneous and heterogeneous binding assays to provide a detectable signal. However, an accurate detection of fluorescent signals produced by analytes bound to the labels is often hindered by a high and variable background due to the fluorescence of the biological sample itself.

Liquid flow cytometry helps to overcome this problem. In flow cytometry, labeled particles with bound analyte are passed through a laser beam. The emitted fluorescent signals of the particles are measured and correlated to the presence and quantity of the analyte. The main advantage of this method is its capability of accurate detection and measurement of the fluorescent signals associated with the bound analyte in the presence of other unbound constituents of the sample.

Saccharides represent an important group of biochemical analytes. Current methods for determining their concentrations in a sample typically rely on enzymatic assays. Although enzymatic assays have proven to be reliable, they must utilize rather unstable enzymes, which become exhausted in the presence of their substrates. Additionally, conventional enzymatic assay methods cannot be utilized in a convenient flow cytometry format. Particle-based assays, such as the ones used in flow cytometry, require a signal change confined to the particle. Normal enzymatic analysis methods use freely diffusable intermediates that violate this requirement.

Determination of saccharides is particularly important in clinical settings. Treatment of diabetes and hypoglycemia requires frequent measurement of tissue glucose concentration. This is commonly accomplished by drawing a small blood sample (as by a fingerstick) several times daily. A patient typically uses a lancet to draw a droplet of blood and applies the droplet to a reagent strip which is read in a small meter. This process is painful, invasive, and time-consuming.

Recently, a minimally invasive method for measuring glucose in vivo has been disclosed in U.S. patent application Ser. No. 09/393,738 filed on Sep. 10, 1999, which has been commonly assigned to the assignee of the present invention and is incorporated by reference herein. The method is based on the use of implanted sensor particles capable of generating a detectable analyte signal in response to the analyte concentration in the body. The proposed method is less intrusive than the conventional fingerstick technique for measuring blood D-glucose. It requires only periodical replacement of the sensor particles in the skin.

The sensor particles typically comprise fluorescence sensors either attached to the surface or incorporated into the body of the particles. The sensors are specific to the target analyte. The binding of the sensor to the analyte generates a detectable signal that is responsive to the concentration of the analyte. When the analyte is glucose, diboronic acids conjugated to fluors are used.

Similar fluorescent sensors, which are specific to glucose, are also described by James et al., in the Journal of the American Chemical Society, 1995, vol. 117 pp. 8982–8987, by James et al. in U.S. Pat. No. 5,503, 770, and by Takeuchi et al. in Tetrahedron, vol. 52, No. 4, pp. 1195–1204. Briefly, the fluorescent sensors of James and Takeuchi have the following general formula:

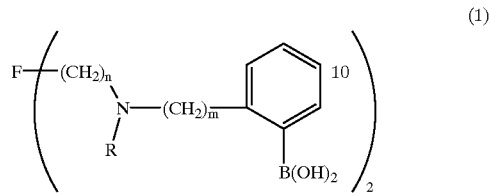

(1)

In the formula, F designates a fluorophore, R is a lower aliphatic or aromatic group, and n+m is 2 or 3. The fluorescent intensity of the sensor changes in response to photo-induced electron transfer (PET) between the amine group and the fluorophore as modulated by binding of glucose hydroxyls to a pair of boronic acids. In the absence of glucose binding, the fluorescence by the fluorescent group is quenched by the unshared electron pair of the nitrogen atom. When glucose is bound, the unshared electron pair is utilized in the bond formation and does not participate in fluorescence-quenching. Consequently, intrinsic fluorescence of the sensor is expressed.

SUMMARY OF THE INVENTION

While an application of above-described fluorescent sensors in biochemical assays and clinical tests provide certain advantages over earlier enzyme-based in vitro methods, it, nevertheless, suffers from serious shortcomings. Because the fluorophore is used as a spacer to separate the saccharide binding groups and to provide desired analyte selectivity, strict limitations on the type of the fluorophore, its size and conformation are imposed. For the same reason, there are also significant limitations on the type, size, and conformation of analyte that can specifically bind to the disclosed fluorescent compounds to produce a detectable signal. Furthermore, although the referenced art suggests using the PET-type fluorescent compounds in a heterogeneous assay format, no means for attaching the compound to a solid support are provided. Again, such attachment would be particularly difficult in view of the strict limitations imposed on the conformation and structure of the fluorescent molecule.

Accordingly, it is an object of the present invention to provide a fluorescent sensor, particularly PET-type sensor, with a modular structure, which allows independent selection of fluorescent and binding groups. It is also an object of the present invention to provide a fluorescent sensor that can be easily adapted for specific binding to a broad range of analytes. It is a further object of the present invention to provide a fluorescent sensor that can be used in both homogeneous and heterogeneous binding assay formats and can be easily attached to solid surfaces. Finally, it is an object of the present invention to provide convenient methods of making and using the fluorescent sensors.

These and other objects and advantages are achieved in a modular fluorescence sensor of the present invention having the following general formula:

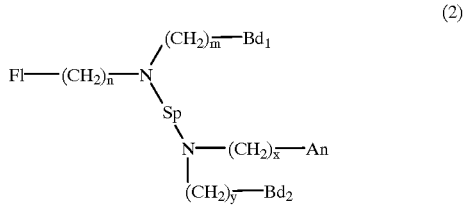

(2)

In the above formula, Fl is a fluorohore, N is a nitrogen atom, Bd1 and Bd2 are independently selected binding groups, Sp is an aliphatic spacer, and An is an anchor group for attaching the sensor to solid substrates. n=1 or 2, m=1 or 2, and x is an integer. The binding groups are capable of binding an analyte molecule to form a stable 1:1 complex. Examples of binding groups include, but are not limited to, boronic acid, crown ether, and aza-crown ether, such as 1,4,7,10,13-Pentaoxa-16-aza-cyclooctadecane (aza 18-crown-6) and 1,4,7,13-tetraoxa-10-aza-cyclohexadecane (aza 15-crown-5). In a preferred embodiment, the Bd1 is R1—B(OH)2 and Bd2 is R2—B(OH)2. R1 and R2 are aliphatic or aromatic functional groups selected independently from each other and B is a boron atom.

In another aspect, the present invention provides a method of synthesizing a modular fluorescence sensor. The method comprises the steps of:

(a) forming an asymmetric compound of the following general formula:

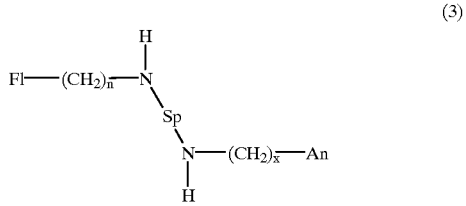

(3)

and (b) replacing hydrogen atoms with $B_{d1}$ and $B_{d2}$ groups.

In the above formula, Fl is a fluorophore, N is a nitrogen atom, H is a hydrogen atom, Sp is an aliphatic spacer, and An is an anchor group for attaching the sensor to solid substrates. $B_{d1}$ and $B_{d2}$ are independently selected binding groups capable of binding an analyte molecule to form a stable 1:1 complex, n=1 or 2, and x is an integer.

The present invention also provides a method of labeling solid substrates. The method comprises the steps of:

(a) providing a solid substrate;

(b) providing a modular fluorescence sensor of the present invention of formula (2), wherein An is capable of being attached to the solid substrate;

(c) reacting the sensor with the solid substrate under a condition sufficient to attach the sensor to the substrate.

The solid substrate may be a micro particle. The sensor may be attached to the outer surface of the particle or it may be bound to the inside of the particle.

The modular fluorescence sensor of the present invention has been found to provide a number of advantages. The modular structure of the sensor allows a convenient replacement of its functional parts to fit analytes within a broad range of structures, binding affinities, and solubilities. The anchor site and the asymmetrical structure of the instant sensor permit a convenient attachment of the sensor to a variety of solid substrates, as required in heterogenic assay formats. Also, the fluorescent sensor of this invention couples the signal generation to the analyte binding and thereby localizes the measurement of an analyte. Consequently, the sensor is well suited for applications in particle-based assays and flow cytometry. Finally, in the present invention, a special spacer group is used to provide the desired intramolecular distance between analyte-binding groups, which governs the analyte selectivity. The conventional PET-type sensors, on the other hand, utilize a fluorophore as a spacer, which puts stringent limitations on the type of fluorophore that can be used. On the contrary, in the present invention, the fluorophore may be selected without limitations to its size or conformation.

In view of its versatility, the novel fluorescent sensor of the present invention is useful in a broad range of analytical and clinical applications. The sensor is particularly beneficial in the detection and qualitative analysis of saccharides.

DESCRIPTION OF THE FIGURES

The above-mentioned and other features of this invention and the manner of obtaining them will become more apparent, and will be best understood by reference to the following description, taken in conjunction with the accompanying drawings. These drawings depict only typical embodiments of the invention and do not therefore limit its scope.

DETAILED DESCRIPTION OF THE INVENTION

Figure 1:
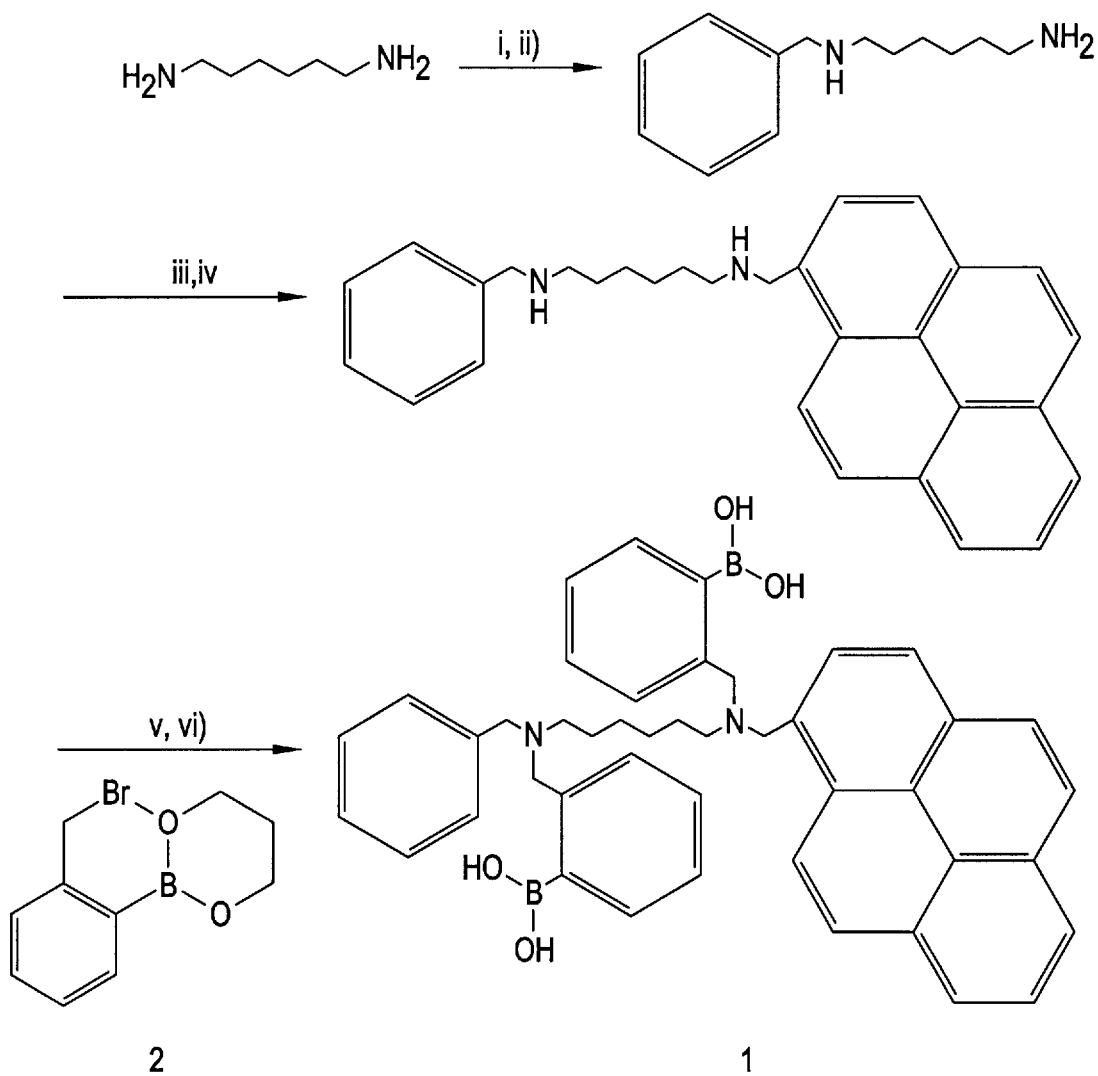
FIG. 1 shows a synthetic scheme for a fluorescent sensor of the present invention.

The present invention provides a modular fluorescence sensor having the following general formula:

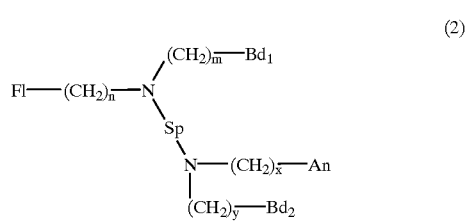

(2)

In the above formula, Fl is a fluorophore, N is a nitrogen atom, $B_{d1}$ and $B_{d2}$ are independently selected binding groups, Sp is an aliphatic spacer, and An is an anchor group for attaching the sensor to solid substrates. In the formula (2), n, m, x, and y are integers, where n=1 or 2, m=1 or 2, and y=1 or 2, and x is an integer. In one embodiment, x=0–10. The binding groups are capable of binding an analyte molecule to form a stable 1:1 complex.

In the present invention, the fluorophore Fl does not act as a spacer between binding groups. Consequently, it can be selected from a broad range of functional groups having various sizes and conformations. Examples of acceptable fluorophores include, but are not limited to, functional groups containing π-electron systems, such as naphtyl, anthryl, pyrenyl, phenanthryl, and perylenyl. The fluorophore may be unsubstituted or substituted. For example, it is well known that certain molecules can be rendered water-soluble by the introduction into the molecule of a strong basic or acidic group, such as carboxylic acid or sulfonic acid. Consequently, the fluorophore may be substituted with sulfonic acid group(s) to accommodate homogeneous assay formats.

Although the sensor of the present invention contains a fluorophore in its molecular structure, it does not emit fluorescence in the absence of the analyte. As explained in the Introduction, in PET molecules, the fluorescence of the fluorophore is quenched by the unshared electron pair of the nitrogen atom(s). When the sensor binds the analyte contained in a sample, the unshared electron pair of the nitrogen atom participates in the formation of an intramolecular complex of the sensor and the analyte. Consequently, the intrinsic fluorescence of the sensor becomes expressed.

In the present invention, the binding groups may be any functional groups, as long as they provide the desired specific binding of the analyte to the sensor with a formation of 1:1 complex. The binding groups are preferably electron deficient groups. The electron deficiency governs the shift of the unshared electron pair from the nitrogen atoms to the binding group when, specifically binding the analyte. Examples of the acceptable binding groups include, but are not limited to, boronic acid, crown ether, and aza-crown ether, such as 1,4,7,10,13-Pentaoxa-16-aza-cyclooctadecane (aza 18-crown-6) and 1,4,7,13-tetraoxa-10-aza-cyclohexadecane (aza 15-crown-5). Examples of analytes that may be identified by utilizing sensors of the present invention include, but are not limited to, saccharides, amino saccharides, and carbonyl saccharides.

In a preferred embodiment, the $B_{d1}$ is $R_1$—$B(OH)_2$ and $B_{d2}$ is $R_2$—$B(OH)_2$. $R_1$ and $R_2$ are aliphatic or aromatic functional groups selected independently from each other, and B is a boron atom. Examples of acceptable R1 and R2 groups include, but are not limited to, methyl, ethyl, propyl, butyl, phenyl, methoxy, ethoxy, butoxy, and phenoxy groups.

The binding groups are separated by the aliphatic spacer Sp. The length of the carbon backbone of the spacer is selected to match the size of the analyte. In one embodiment, where the analyte is glucose, the length of the carbon backbone is such that distance between binding groups is comparable with the size of glucose.

Although the spacer may have a straight, branched, or cyclic structure, in the preferred embodiment the spacer is a straight-chain alkane. Typically, the spacer comprises from 1 to 9 carbon atoms, but spacers of larger length may be also used to match the size of the analyte. For example, when the analyte is glucose, the spacer may comprise six carbon atoms.

The anchor group An of the sensor provides means for immobilization of the sensor on a solid support, for example on a support used in heterogeneous binding assay. The An group is attached to one of the nitrogen atoms of the sensor either directly or by means of a carbon bridge —$(CH_2)_x$—. The type of An group and the number of carbons (x) in the carbon bridge are selected to provide a secure attachment of the sensor to the solid support. For example, in one embodiment, the sensor is attached to a micrometer scale particle. The micrometer scale particles with the attached sensor of the present invention may be used in various applications, including flow cytometry. Typically, An comprises an organic functionality. In one embodiment An comprises phenyl.

The anchor group An is optional. For example, in homogeneous assays, no attachment of the sensor is required. Therefore, the sensor may be synthesized without anchor group or with a functional group, such as methyl and benzyl.

This invention provides a framework for modular sensors that have a minimal interaction between their functional elements. Individual functional elements of the sensor of the present invention may be easily replaced to accommodate a broad range of analytes. For example, in one embodiment, all functional groups of the sensor and the length of carbon bridges are selected to provide selective binding of the sensor to glucose.

Preferably, a modular fluorescence sensor of the present invention has the following general formula:

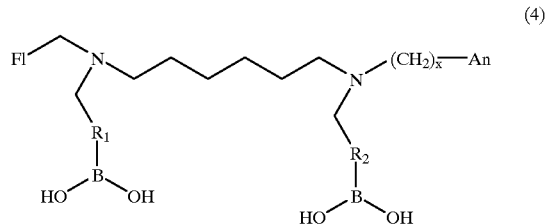

(4)

In the above formula (4), Fl is a fluorophore, N is a nitrogen atom, and B is a boron atom. $R_1$ and $R_2$ are aliphatic or aromatic functional groups which allow covalent binding of an analyte with the hydroxyls of boronic acid functionalities to form a stable 1:1 complex. $R_1$ and $R_2$ are selected independently from each other. An is an anchor group for attaching the sensor to a solid substrates; and x is any integer. In one embodiment, x=0–10.

A typical compound falling within the formulas (2) and (4) of the present invention has the following formula:

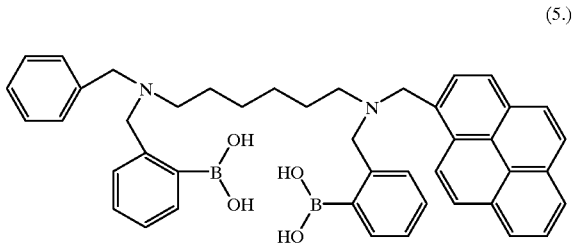

(5.)

Unexpectedly, the compound (5) has a specific sensitivity to glucose and emits a strong fluorescence when binding to glucose contained in a sample. Such specificity to glucose can be explained by the structure of the compound (5). Two boronic acid groups are separated from each other by a spacer comprising a six-carbon chain, which allows them to bind cis-1,2- and 4,6-hydroxyl groups of glucose and form a strong 1:1 complex with glucose.

In another aspect, the present invention provides a method of synthesizing a modular fluorescence sensor. The method comprises the steps of:

(a) forming an asymmetric compound of the following general formula:

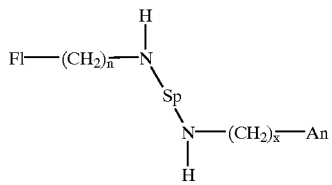

(3)

and (b) replacing hydrogen atoms with $B_{d1}$ and $B_{d2}$ groups.

In the above formula, Fl is a fluorophore, N is a nitrogen atom and H is a hydrogen atom, Sp is an aliphatic spacer, and An is an anchor group for attaching the sensor to solid substrates. $B_{d1}$ and $B_{d2}$ are independently selected binding groups capable of binding an analyte molecule to form a stable 1:1 complex, n=1 or 2, and x is any integer. In one embodiment, x=0–10. In one embodiment, the step of replacing hydrogen atoms comprises adding orthobromomethyl phenylboronic acid.

For instance, a reaction scheme such as one shown in FIG. 1 and discussed in detail in Example 1 below may be utilized.

The present invention also provides a method of labeling solid substrates. The method comprises the steps of:

(a) providing a solid substrate;
(b) providing a modular fluorescence sensor of the present invention of formula (2), wherein An is capable of being attached to the solid substrate;
(c) reacting the sensor with the solid substrate under a condition sufficient to attach the sensor to the substrate.

For the purpose of the present invention, a condition is sufficient if it does not hinder attachment of the sensor to the substrate. Those skilled in the art will know what conditions should be sufficient based on the type of the solid substrate and the nature of the anchor group. For example, when the anchor group is amino, preferably primary amine, the solid substrate should contain carboxylic acid group, and the sufficient condition is satisfied by addition of a coupling agent. Acceptable coupling agents include, but are not limited to, 1,3-dicyclohexylcarbodiimide (DCC), 1-ethyl-3-(3-dimethylaminopropyl)carboimide or water soluble carboimide, and carbonyldiimidazole (CDI). Additionally, N-hydroxysuccinimide may be added to the reaction mixture to obtain better reaction efficiency. In accordance with one embodiment of the present invention, when the anchor group is primary amine, the sensor is attached to the substrate by mixing 1,3-disopropylcarbodiimide (DIPC), 1-hydroxy-1H-benzotriazole (HOBt), 4-N,N-dimethylaminopyridine (DMAP) with N,N-dimethylformamide (DMF) as solvent, and stirring the mixture at room temperature for 2–24 hours.

The solid substrate may be a micro particle. In one embodiment of the present invention, the particles are in a size range from about 0.1 to about 20 micrometers.

The particles are preferably round and uniform, such as commonly available polystyrene latex particles formed by emulsion polymerization. They may be produced of other materials and by other processes that are known in the art. Examples of the materials and methods include, but are not limited to, plasticized polyvinyl chloride (PVC) particles produced by droplet casting of dissolved polymers or glass-like particles produced from sol gels. In addition, the sensor particles may be made of a bio-resorbable polymer. Examples of a bio-resorbable polymer include, but are not limited to, polyglycolic acid (PGA), poly-DL-lactide-co-glycolide (PLGA), starch, gelatin, and the like.

The sensor particle of the present invention may be a hydrophilic particle such as, but not limited to, controlled pore glass (CPG) beads or a polymer gel. It may also be a hydrophobic particle with appropriate plasticizers or a sufficiently low glass transition temperature to permit free permeation by small analytes. Alternatively, it may be a semipermeable membrane such as, but not limited to, a liposome. To avoid the degradation of the sensor, the sensor may be bound to the inside of a hydrophilic particle, such as pores of CPG beads or a polymer gel. The receptors may also be captured inside a hydrophobic particle with appropriate plasticizers to permit free permeation by small analytes. The receptor may further be packaged inside the semipermeable membrane. For the purpose of the present invention, a plasticizer is appropriate if it permits free permeation of small analytes into a hydrophobic particle. Examples of such a plasticizer include, but are not limited to, dioctyl adipate, diisodecyl adipate, and the like. In accordance with an alternative embodiment, a sensor of the present invention may also be bound to the surface of hydrophobic or other insoluble particles.

The foregoing is meant to illustrate, but not to limit, the scope of the invention. Indeed, those of ordinary skill in the art can readily envision and produce further embodiments, based on the teachings herein, without undue experimentation.

EXAMPLE 1

The fluorescent sensor of the formula (5) is prepared in accordance with the synthetic routes as shown in FIG. 1 and as described in detail below.

Preparation of N-benzyl-hexane-1,6-diamine

A solution of hexamethlene-1,6-diamine (17.15 g, 148 mmol) and benzaldehyde (3.0 ml, 29.5 mmol) in tetrahydrofuran (THF) (300 ml) and ethanol (75 ml) was stirred at room temperature for 24 hours under a nitrogen atmosphere. The solvent was removed and the oil was dried under vacuum. The dried residue was dissolved in THF (100 ml) and sodium borohydride (5.58 g, 148 mmol) was added to the solution. The solution was stirred at room temperature for 7 hours under nitrogen atmosphere. Methanol and water were added to the solution and the solvents were removed under vacuum. The obtained oil was dissolved in chloroform, and washed with water. The solution was dried over magnesium sulphate and the solvent was then removed under vacuum to give a colorless oil (4.49 g, 74%). $^{1}$H NMR (CDCl$_{3}$) δ/ppm 1.1–1.5 (8H, m, (CH$_{2}$)$_{4}$), 2.55 (2H, t, NHCH$_{2}$), 2.65 (2H, t, ArCNCH$_{2}$), 3.75 (2H, s, ArCH$_{2}$), 7.1–7.25 (5H, m, ArH).

Preparation of N-benzyl-N'-pyren-1-ylmethylene-hexane-1,6-diamine

A solution of N-benzyl-hexane-1,6-diamine (500 mg, 2.42 mmol) and 1-pyrenecalboxaldehyde (670 mg, 2.90 mmol) in THF and methanol (12.5 ml each) was stirred at room temperature for 20 hours under a nitrogen atmosphere. The solvent was removed under vacuum, and the residue was washed with methanol. The precipitate was filtered off, the filtrate was removed and dried under vacuum to give a yellow oil (940 mg, 93%). $^1$H NMR (CDCl$_3$) δ/ppm 1.45–1.62 (6H, m, (CH$_2$)$_3$), 1.85 (2H, m, =HCCH$_2$), 2.65 (2H, t, NHCH$_2$), 3.78 (2H, s, PhCH$_2$), 3.85 (2H, t, =NCH$^2$), 7.15–7.25 (5H, m, Ph-H), 7.95–8.23, 8.53, 8.88 (7H, 1H, 1H respectively, m, d, d, Py-H), 9.27 (1H, s, N=CH). $^{13}$C NMR (CDCl$_3$) δ/ppm 27.31, 27.49, 30.12, 31.16, 49.50, 54.13, 62.77, 122.64, 125.00, 125.59, 125,84, 126.12, 126.24, 126.91, 127.50, 128.16, 128.42, 128.59, 130.64, 131.30, 140.50, 159.54; m/z (TOF) 419 ([M+H]$^+$, 100%).

Preparation of N-benzyl-N'-pyren-1-ylmethyl-hexane-1.6-diamine

A solution of N-benzyl-N'-pyren-1-ylmethylene-hexane-1,6-diamine (420 mg, 1.00 mmol) and sodium borohydride (190 mg, 5.00 mmol) in methanol (10.0 ml) was stirred at room temperature for 3 hours under a nitrogen atmosphere. The solvent was removed under vacuum, and the residue was dissolved in chloroform and washed with water, and dried over magnesium sulphate. The solvent was removed and the residue was dried under vacuum to give a yellow oil (386/mg, 92%). $^1$H NMR (CDCl$_3$) δ/ppm 1.32 (4H, m, (CH$_2$)$_2$), 1.45 (2H, m, BnNCCH$_2$), 1.55 (2H, m, PyCNCCH$_2$), 2.55 (2H, t, BnNCH$_2$), 2.75 (2H, t, PyCNCH$_2$), 3.75 (2H, s, PhCH$_2$), 4.50 (2H, s, PyCH$_2$), 7.15–7.25 (5H, m, Ph-H), 7.95–8.10, 8.15–8.22, 8.37 (4H, 4H, 1H respectively, m, m, d, Py-H). $^{13}$C NMR (CDCl$_3$) δ/ppm 27.35, 30.16, 49.46, 50.02, 51.94, 54.13, 54.13, 123.19, 124.72, 125.00, 125.09, 125.89, 126.89, 127.03, 127.50, 127.64, 128.14, 128.40, 129.06, 131.34, 134.15; m/z (EI) 420 ([M])$^+$, 7%).

Preparation of N-benzyl-N,N'-bis-(2-boronobenzyl)-N'-pyren-1ylmethyl-hexane-1,6-diamine (FIG. 1, compound 1 or formula (5)).

A solution of N-pyren-1-ylmethyl-hexame-1,6-diamine (291 mg, 0.69 mmol), 2-(2-bromomethyl-phenyl)-[1, 3, 2]dioxaborinane (422 mg, 1.66 mmol), and potassium carbonate (380 mg, 2.76 mmol) in dry acetonitril (10 ml) was heated at reflux for 20 hours under nitrogen atmosphere. The solvent was removed under vacuum, the residue was dissolved in chloroform and washed with water. The solvent was dried over magnesium sulphate and removed under vacuum. The residue was dissolved in THF (10 ml). Water (10 ml) was added to the THF solution, and the solution was stirred at room temperature for 3 hours. Organic phase was extracted with chloroform, washed with water, and dried over magnesium sulphate. The solvent was removed under vacuum. The residue was reprecipitated from chloroform with n-hexane to give a white yellow powder (172 mg, 35%). $^1$H NMR (CDCl$_3$) δ/ppm 1.25–1.48 (8H, m, (CH$_2$)$_4$), 2.25 (2H, t, BnNCH$_2$), 2.48 (2H, t, PyCNCH$_2$), 3.45 (2H, s, PhB(OH)CH$_2$NBn), 3.58 (2H, s, PhB(OH)CH$_2$NCPy), 3.85 (2H, s, PhCH$_2$), 4.21 (2H, s, PyCH$_2$), 7.02–7.41 and 7.88–8.19 (22H, m, Ar—H), 8.86 (4H, bs, BOH). $^{13}$C NMR (CDCl$_3$) δ/ppm 51.69, 52.99, 54.42, 56.42, 57.11, 61.03, 61.86, 67.85, 122.90, 124.55, 124.99, 125.79, 127.31, 128.28, 128.57, 129.43, 130.00, 130.55, 136.32, 141.56; Found: C, 76.56; H, 6.69; N, 3.80, C$_{44}$H$_{46}$B$_2$N$_2$O$_4$ requires C, 76.76; H, 6.73; N, 4.07%; m/z (FAB) 1230 ([M+H+4(3-HOCH$_2$C$_6$H$_4$NO$_2$)-4(H$_2$O)]+, 100%) mp. 165–168° C.

EXAMPLE II

Figure 2:
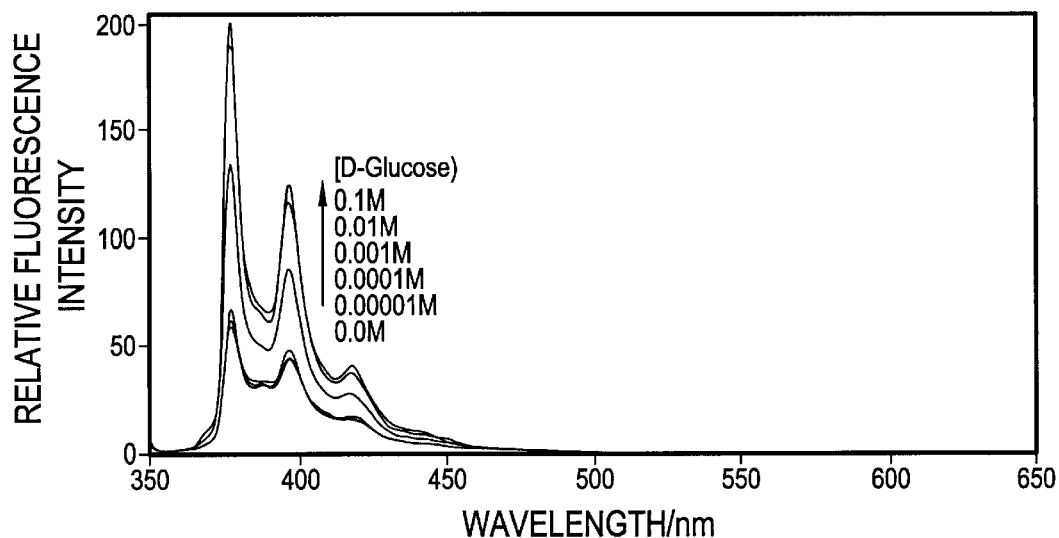
FIG. 2 shows the response of the fluorescent spectrum to changing concentrations of D-glucose.

A relative fluorescent intensity of the sensor of formula (5), as prepared in EXAMPLE I, was measured in 52.1 wt % methanol and phosphate buffer (pH 8.21) with various D-glucose concentrations (FIG. 2). Phosphate buffer was prepared as described in D. D. Perrin, and B. Dempsey, *Buffers for pH and Metal Ion Control*, Chapman and Hall, London, 1974. The fluorescence spectra were recorded as increasing amounts of D-glucose were added to the solution. The mixture solutions were measured excitation at 342 nm. The fluorescent intensity was found to correlate with total D-glucose concentration in the solution.

Figure 3:
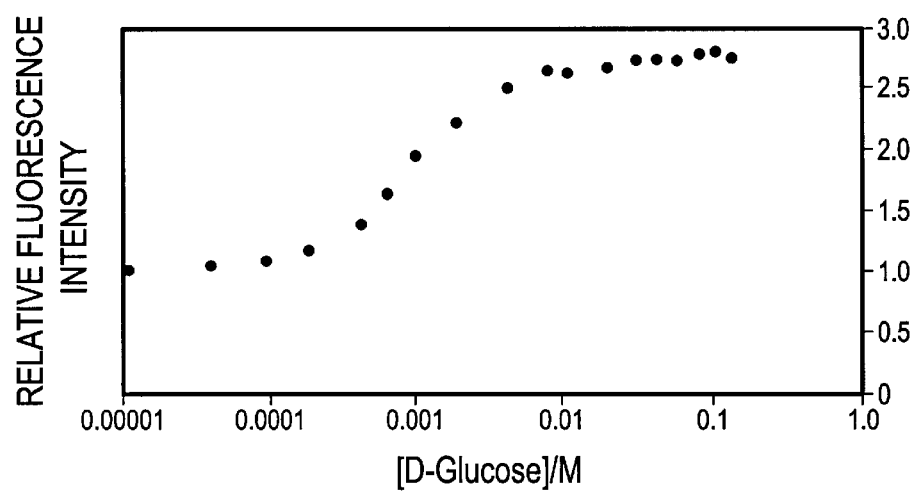
FIG. 3 depicts a plot of logarithm of D-glucose concentration versus fluorescence intensity.

FIG. 3, shows a plot of logarithm of D-glucose concentration versus fluorescence intensity. The plot demonstrates that the fluorescence increases as the D-glucose concentration increases, and that the fluorescence of the PET receptor may be used to assay D-glucose concentration.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description.

What is claimed is:

1. A modular fluorescence sensor having the following general formula:

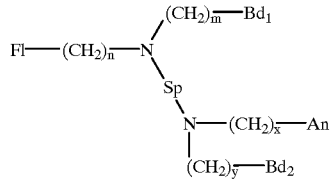

wherein:

Fl is a fluorophore;

N is a nitrogen atom;

B$_{d1}$ and B$_{d2}$ are independently selected binding groups, wherein the binding groups are capable of binding an analyte molecule to form a stable 1:1 complex;

Sp is an aliphatic spacer;

An is an anchor group for attaching the sensor to a solid substrate; and n, m, x and y are integers, where n=1 or 2, m=1 or 2, and y=1 or 2, x is an integer.

2. The sensor of claim 1, wherein Fl is selected from the group consisting of naphtyl, anthryl, pyrenyl, phenanthryl, and perylenyl.

3. The sensor of claim 1, wherein B$_{d1}$ is R$_1$—B(OH)$_2$ and B$_{d2}$ is R$_2$—B(OH)$_2$, wherein R$_1$ and R$_2$ are aliphatic or aromatic functional groups selected independently from each other and B is a boron atom.

4. The sensor of claim 3, wherein R$_1$ and R$_2$ selected from the group consisting of: methyl, ethyl, propyl, butyl, phenyl, methoxy, ethoxy, butoxy, and phenoxy groups.

5. The sensor of claim 1, wherein Sp is a straight-chain alkane.

6. The sensor of claim 5, wherein the straight-chain alkane comprises from 1 to 9 carbon atoms.

7. The sensor of claim 6, wherein the straight-chain alkane comprises 6 carbon atoms.

8. The sensor of claim 1, wherein An comprises organic functionality.

9. The sensor of claim 8, wherein An comprises methyl.

10. The sensor of claim 8, wherein An comprises phenyl.

11. The sensor of claim 1, wherein An and x are selected to provide stable attachment of the sensor to a micrometer scale particle.

12. The sensor of claim 11, wherein the particles are suitable for use in flow cytometry.

13. The sensor of claim 1, wherein $B_{d1}$, $B_{d2}$, Sp, m, and y are chosen to provide selective binding of the sensor to glucose.

14. A modular fluorescence sensor having the following general formula:

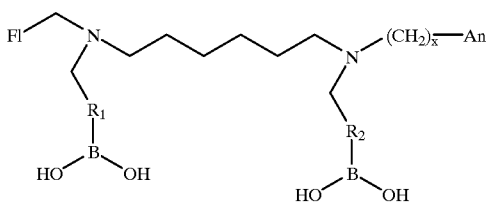

wherein:

Fl is a fluorophore;

N is a nitrogen atom and B is a boron atom;

$R_1$ and $R_2$ are aliphatic or aromatic functional groups which allow covalent binding of an analyte to the hydroxyl groups forming a stable 1:1 complex, wherein $R_1$ and $R_2$ are selected independently from each other and;

An is an anchor group for attaching the sensor to a solid substrate; and x is an integer.

15. The sensor of claim 14, wherein Fl is selected from the group consisting of naphtyl, anthryl, pyrenyl, phenanthryl, and perylenyl.

16. The sensor of claim 14, wherein $R_1$ and $R_2$ are independently selected from the group consisting of: methyl, ethyl, propyl, butyl, phenyl, methoxy, ethoxy, butoxy, and phenoxy groups.

17. The sensor of claim 14, wherein An comprises organic functionality.

18. The sensor of claim 17, wherein An comprises methyl.

19. The sensor of claim 17, wherein An comprises phenyl.

20. The sensor of claim 14, wherein An and x are selected to provide stable attachment of the sensor to a micrometer scale particle.

21. A modular fluorescence sensor of the following formula:

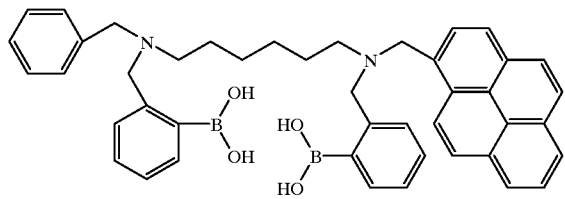

22. A composition comprising:

a modular fluorescence sensor having the following general formula:

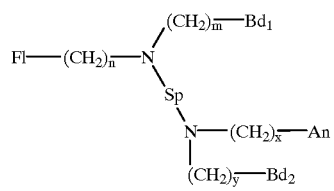

wherein:

Fl is a fluorophore;

N is a nitrogen atom;

$B_{d1}$ and $B_{d2}$ are independently selected binding groups, wherein the binding groups are capable of binding an analyte molecule to form a stable 1:1 complex;

Sp is an aliphatic spacer;

An is an anchor group for attaching the sensor to a solid substrate; and n, m, x and y are integers, were n=1 or 2, m=1 or 2, and y=1 or 2, x is an integer; and an analyte bound to the sensor.

23. The composition of claim 22, wherein the analyte is selected from a group comprising saccharides, amino saccharides, and carbonyl saccharides.

24. The composition of claim 22, wherein the Sp comprises six carbon atoms and the analyte is glucose.

25. The composition of claim 22, wherein the modular fluorescence sensor has the following general formula:

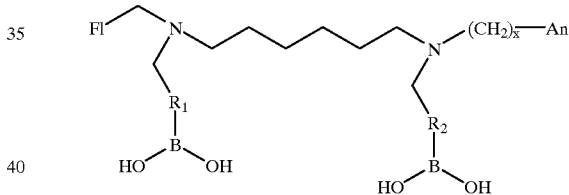

wherein:

B is a boron atom; and $R_1$ and $R_2$ are aliphatic or aromatic functional groups which allow covalent binding of an analyte to the hydroxyl groups forming a stable 1:1 complex, wherein $R_1$ and $R_2$ are selected independently from each other.

26. The composition of claim 22, wherein the analyte is glucose and the modular fluorescence sensor has the following general formula:

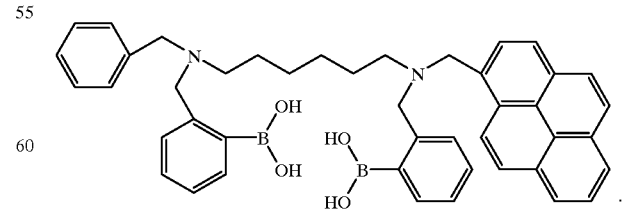

27. A composition comprising:

a modular fluorescence sensor having the following general formula:

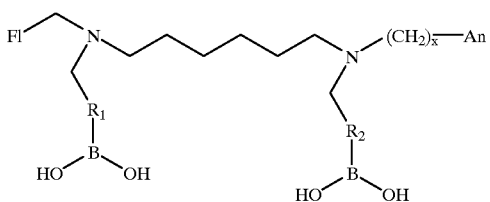

wherein:
 Fl is a fluorophore;
 N is a nitrogen atom;
 B is a boron atom;
 R₁ and R₂ are aliphatic or aromatic functional groups which allow covalent binding of an analyte to the hydroxyl groups forming a stable 1:1 complex, wherein R₁ and R₂ are selected independently from each other;

An is an anchor group for attaching the sensor to a solid substrate; and
 x is an integer; and
 glucose bound to the sensor.

28. The composition of claim 27, wherein the modular fluorescence sensor has the following general formula:

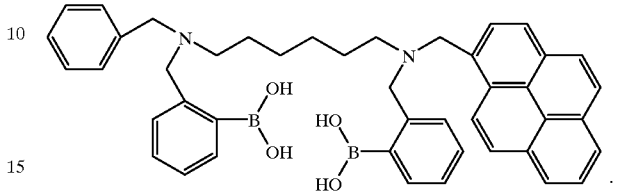

* * * * *